United States Patent
Li et al.

(10) Patent No.: US 8,350,914 B2
(45) Date of Patent: Jan. 8, 2013

(54) SYSTEMS AND METHODS FOR ON-LINE MARKER-LESS CAMERA CALIBRATION USING A POSITION TRACKING SYSTEM

(75) Inventors: Dun Alex Li, Salem, NH (US);
Christopher Allen Nafis, Rexford, NY (US)

(73) Assignee: General Electric Company, Schenectady, NY (US)

(*) Notice: Subject to any disclaimer, the term of this patent is extended or adjusted under 35 U.S.C. 154(b) by 8 days.

(21) Appl. No.: 13/101,776

(22) Filed: May 5, 2011

(65) Prior Publication Data
US 2011/0211076 A1 Sep. 1, 2011

Related U.S. Application Data

(63) Continuation of application No. 11/465,595, filed on Aug. 18, 2006, now Pat. No. 8,022,990.

(51) Int. Cl.
*H04N 17/00* (2006.01)
(52) U.S. Cl. ............... 348/187; 348/188; 348/180
(58) Field of Classification Search ............ 348/187, 348/188, 180; 600/424; *H04N 17/00*
See application file for complete search history.

(56) References Cited

U.S. PATENT DOCUMENTS

| | | | |
|---|---|---|---|
| 5,923,727 A | 7/1999 | Navab | |
| 6,201,882 B1 | 3/2001 | Tanaka | |
| 6,437,823 B1 | 8/2002 | Zhang | |
| 6,490,475 B1 | 12/2002 | Seeley et al. | |
| 6,776,526 B2 | 8/2004 | Zeiss | |
| 7,085,400 B1 | 8/2006 | Holsing et al. | |
| 7,097,357 B2 | 8/2006 | Johnson et al. | |
| 7,352,388 B2 | 4/2008 | Miwa et al. | |
| 8,022,990 B2 * | 9/2011 | Li et al. ............ 348/187 | |

* cited by examiner

*Primary Examiner* — Trang U Tran
(74) *Attorney, Agent, or Firm* — McAndrews, Held & Malloy, Ltd.; William Baxter

(57) ABSTRACT

Certain embodiments of the present invention provide methods and systems for calibration of an imaging camera or other image acquisition device. Certain embodiments include characterizing a transformation from a coordinate system of an imager to a coordinate system of a first sensor positioned with respect to the imager using a first off-line calibration. Certain embodiments also include characterizing a transformation from a coordinate system of an imaging camera source to a coordinate system of a second sensor positioned with respect to the imaging camera source using a second off-line calibration. Additionally, certain embodiments include quantifying intrinsic parameters of the imaging camera source based on a transformation from the coordinate system of the imager to the coordinate system of the imaging camera source based on the first and second off-line calibrations and information from the first and second sensors and a transmitter positioned with respect to an object being imaged.

23 Claims, 7 Drawing Sheets

SYSTEMS AND METHODS FOR ON-LINE MARKER-LESS CAMERA CALIBRATION USING A POSITION TRACKING SYSTEM

RELATED APPLICATIONS

This application claims priority to, and is a continuation of U.S. patent application Ser. No. 11/465,595, filed on Aug. 18, 2006, which is herein incorporated by reference in its entirety.

FEDERALLY SPONSORED RESEARCH OR DEVELOPMENT

Not Applicable

MICROFICHE/COPYRIGHT REFERENCE

Not Applicable

BACKGROUND OF THE INVENTION

The present invention generally relates to imaging and image-guided navigation. In particular, the present invention relates to a system and method for improved calibration of equipment used in imaging and image-guided operations.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and one known position or orientation parameter, a position and orientation calculation may determine position and orientation information for each of the transmitter coils with respect to the receiver coil trio with three degrees of freedom.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery involve very precise planning and control for placement of an elongated probe or other article in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as MRI, PET or CT scan images, which provide accurate tissue images. For placement of pedicle screws in the spine, where visual and fluoroscopic imaging directions may not capture an axial view to center a profile of an insertion path in bone, such systems have also been useful.

When used with existing CT, PET or MRI image sets, previously recorded diagnostic image sets define a three dimensional rectilinear coordinate system, either by virtue of their precision scan formation or by the spatial mathematics of their reconstruction algorithms. However, it may be desirable to correlate the available fluoroscopic views and anatomical features visible from the surface or in fluoroscopic images with features in the 3-D diagnostic images and with external coordinates of tools being employed. Correlation is often done by providing implanted fiducials and adding externally visible or trackable markers that may be imaged. Using a keyboard or mouse, fiducials may be identified in the various images. Thus, common sets of coordinate registration points may be identified in the different images. The common sets of coordinate registration points may also be trackable in an automated way by an external coordinate measurement device, such as a suitably programmed off-the-shelf optical tracking assembly. Instead of imageable fiducials, which may for example be imaged in both fluoroscopic and MRI or CT images, such systems may also operate to a large extent with simple optical tracking of the surgical tool and may employ an initialization protocol wherein a surgeon touches or points at a number of bony prominences or other recognizable anatomic features in order to define external coordinates in relation to a patient anatomy and to initiate software tracking of the anatomic features.

Generally, image-guided surgery systems operate with an image display which is positioned in a surgeon's field of view and which displays a few panels such as a selected MRI image and several x-ray or fluoroscopic views taken from different angles. Three-dimensional diagnostic images typically have a spatial resolution that is both rectilinear and accurate to within a very small tolerance, such as to within one millimeter or less. By contrast, fluoroscopic views may be distorted. The fluoroscopic views are shadowgraphic in that they represent the density of all tissue through which the conical x-ray beam has passed. In tool navigation systems, the display visible to the surgeon may show an image of a surgical tool, biopsy instrument, pedicle screw, probe or other device projected onto a fluoroscopic image, so that the surgeon may visualize the orientation of the surgical instrument in relation to the imaged patient anatomy. An appropriate reconstructed CT or MRI image, which may correspond to the tracked coordinates of the probe tip, may also be displayed.

Among the systems which have been proposed for effecting such displays, many rely on closely tracking the position and orientation of the surgical instrument in external coordinates. The various sets of coordinates may be defined by robotic mechanical links and encoders, or more usually, are defined by a fixed patient support, two or more receivers such as video cameras which may be fixed to the support, and a plurality of signaling elements attached to a guide or frame on the surgical instrument that enable the position and orientation of the tool with respect to the patient support and camera frame to be automatically determined by triangulation, so that various transformations between respective coordinates may be computed. Three-dimensional tracking systems employing two video cameras and a plurality of emitters or other position signaling elements have long been commercially available and are readily adapted to such operating room systems. Similar systems may also determine external position coordinates using commercially available acoustic ranging systems in which three or more acoustic emitters are actuated and their sounds detected at plural receivers to determine their relative distances from the detecting assemblies, and thus define by simple triangulation the position and orientation of the frames or supports on which the emitters are mounted. When tracked fiducials appear in the diagnostic images, it is possible to define a transformation between operating room coordinates and the coordinates of the image.

In general, the feasibility or utility of a system of this type depends on a number of factors such as cost, accuracy, dependability, ease of use, speed of operation and the like. Intraoperative x-ray images taken by C-arm fluoroscopes alone have both a high degree of distortion and a low degree of repeatability, due largely to deformations of the basic source and camera assembly, and to intrinsic variability of positioning and image distortion properties of the camera. In an intraoperative sterile field, such devices are typically draped, which may impair optical or acoustic signal paths of the signal elements they employ to track the patient, tool or camera.

More recently, a number of systems have been proposed in which the accuracy of the 3-D diagnostic data image sets is exploited to enhance accuracy of operating room images, by matching these 3-D images to patterns appearing in intraoperative fluoroscope images. These systems may use tracking and matching edge profiles of bones, morphologically deforming one image onto another to determine a coordinate transform, or other correlation process. The procedure of correlating the lesser quality and non-planar fluoroscopic images with planes in the 3-D image data sets may be time-consuming. In techniques that use fiducials or added markers, a surgeon may follow a lengthy initialization protocol or a slow and computationally intensive procedure to identify and correlate markers between various sets of images. All of these factors have affected the speed and utility of intraoperative image guidance or navigation systems.

Correlation of patient anatomy or intraoperative fluoroscopic images with precompiled 3-D diagnostic image data sets may also be complicated by intervening movement of the imaged structures, particularly soft tissue structures, between the times of original imaging and the intraoperative procedure. Thus, transformations between three or more coordinate systems for two sets of images and the physical coordinates in the operating room may involve a large number of registration points to provide an effective correlation. For spinal tracking to position pedicle screws, the tracking assembly may be initialized on ten or more points on a single vertebra to achieve suitable accuracy. In cases where a growing tumor or evolving condition actually changes the tissue dimension or position between imaging sessions, further confounding factors may appear.

When the purpose of image guided tracking is to define an operation on a rigid or bony structure near the surface, as is the case in placing pedicle screws in the spine, the registration may alternatively be effected without ongoing reference to tracking images, by using a computer modeling procedure in which a tool tip is touched to and initialized on each of several bony prominences to establish their coordinates and disposition, after which movement of the spine as a whole is modeled by optically initially registering and then tracking the tool in relation to the position of those prominences, while mechanically modeling a virtual representation of the spine with a tracking element or frame attached to the spine. Such a procedure dispenses with the time-consuming and computationally intensive correlation of different image sets from different sources, and, by substituting optical tracking of points, may eliminate or reduce the number of x-ray exposures used to effectively determine the tool position in relation to the patient anatomy with the reasonable degree of precision.

However, each of the foregoing approaches, correlating high quality image data sets with more distorted shadowgraphic projection images and using tracking data to show tool position, or fixing a finite set of points on a dynamic anatomical model on which extrinsically detected tool coordinates are superimposed, results in a process whereby machine calculations produce either a synthetic image or select an existing data base diagnostic plane to guide the surgeon in relation to current tool position. While various jigs and proprietary subassemblies have been devised to make each individual coordinate sensing or image handling system easier to use or reasonably reliable, the field remains unnecessarily complex. Not only do systems often use correlation of diverse sets of images and extensive point-by-point initialization of the operating, tracking and image space coordinates or features, but systems are subject to constraints due to the proprietary restrictions of diverse hardware manufacturers, the physical limitations imposed by tracking systems and the complex programming task of interfacing with many different image sources in addition to determining their scale, orientation, and relationship to other images and coordinates of the system.

Several proposals have been made that fluoroscope images be corrected to enhance their accuracy. This is a complex undertaking, since the nature of the fluoroscope's 3D to 2D projective imaging results in loss of a great deal of information in each shot, so the reverse transformation is highly underdetermined. Changes in imaging parameters due to camera and source position and orientation that occur with each shot further complicate the problem. This area has been addressed to some extent by one manufacturer which has provided a more rigid and isocentric C-arm structure. The added positional precision of that imaging system offers the prospect that, by taking a large set of fluoroscopic shots of an immobilized patient composed under determined conditions, one may be able to undertake some form of planar image reconstruction. However, this appears to be computationally very expensive, and the current state of the art suggests that while it may be possible to produce corrected fluoroscopic image data sets with somewhat less costly equipment than that used for conventional CT imaging, intra-operative fluoroscopic image guidance will continue to involve access to MRI, PET or CT data sets, and to rely on extensive surgical input and set-up for tracking systems that allow position or image correlations to be performed.

Thus, it remains highly desirable to utilize simple, low-dose and low cost fluoroscope images for surgical guidance, yet also to achieve enhanced accuracy for critical tool positioning.

Magnetic fields may affect x-rays and other image energy sources. Additionally, gravity may affect geometry of an x-ray system. Focal length and piercing point of x-rays may change depending upon the position of a C-arm or other mobile component of an imaging system. A difference between an imaging angle and an angle of the Earth's magnetic field may cause distortion that affects a resulting image. Additionally, an operator or patient may bump the C-arm or other component of an imaging system during operation or positioning, which may affect a resulting image. Thus, there is a need for improved calibration to reduce an effect of distortion on an image.

Registration is a process of correlating two coordinate systems, such as a patient image coordinate system and an electromagnetic tracking coordinate system. Several methods may be employed to register coordinates in imaging applications. "Known" or predefined objects are located in an image. A known object includes a sensor used by a tracking system. Once the sensor is located in the image, the sensor enables registration of the two coordinate systems.

U.S. Pat. No. 5,829,444 by Ferre et al., issued on Nov. 3, 1998, refers to a method of tracking and registration using a headset, for example. A patient wears a headset including radiopaque markers when scan images are recorded. Based on a predefined reference unit structure, the reference unit may then automatically locate portions of the reference unit on the scanned images, thereby identifying an orientation of the reference unit with respect to the scanned images. A field generator may be associated with the reference unit to generate a position characteristic field in an area. When a relative position of a field generator with respect to the reference unit is determined, the registration unit may then generate an appropriate mapping function. Tracked surfaces may then be located with respect to the stored images.

However, registration using a reference unit located on the patient and away from the fluoroscope camera introduces inaccuracies into coordinate registration due to distance between the reference unit and the fluoroscope. Additionally, the reference unit located on the patient is typically small or else the unit may interfere with image scanning A smaller reference unit may produce less accurate positional measurements, and thus impact registration.

Typically, a reference frame used by a navigation system is registered to an anatomy prior to surgical navigation. Registration of the reference frame impacts accuracy of a navigated tool in relation to a displayed fluoroscopic image. Therefore, a system and method that improve registration of the reference frame would be highly desirable. Improved registration may help to decrease error between reference frames and improve navigated tracking accuracy.

Aspects of imaging system variability may be addressed using tracking elements in conjunction with a calibration fixture or correction assembly to provide fluoroscopic images of enhanced accuracy for tool navigation and workstation display. The calibration fixture and use of the calibration fixture in tracking are described in further detail in U.S. Pat. No. 6,484,049 by Seeley et al., issued on Nov. 19, 2002, and U.S. Pat. No. 6,490,475 by Seeley et al., issued on Dec. 3, 2002. A reference unit may also be used, as described in further detail in U.S. Pat. No. 5,829,444 by Ferre et al., issued on Nov. 3, 1998. Radiopaque calibration markers, such as ball bearings (BBs), are used to calibrate components in an imaging system.

Calibration fixtures or reference units may be used to reduce registration error for a registration or reference frame and improve accuracy in navigated tracking of an instrument. A reference frame may include a calibration fixture. The calibration fixture may be removably attached in a precise position with respect to the camera or to the patient. One or more tracking elements or markers may be included in the calibration fixture. A tracking element may be a point-origin defining tracking element that identifies spatial coordinates and/or orientation of the tracking element and, therefore, an object to which the tracking element is attached. Thus, a tracking element may with one or more measurements determine a position of markers in the calibration fixture and a position and orientation of the fixture itself or a surface to which the fixture is attached.

Current fixtures use very radiopaque, discrete markers in radiolucent material. Thus, a need exists for improved calibration fixtures and calibration markers. Typically, an array of discrete, dark markers, such as ball bearings, is arranged in multiple planes for use in calibration. A calibration system watches for spikes and attenuations in a recorded curve to identify the ball bearings in the image.

Examples of calibration fixtures are described in U.S. Pat. No. 5,829,444, mentioned above, and a U.S. patent application entitled "Method and System for Improved Correction of Registration Error in a Fluoroscopic Image", by Douglas Johnson and Lewis Levine, filed on Jun. 2, 2004 (Ser. No. 10/859,767), which is herein incorporated by reference. FIG. 1 illustrates an example of a calibration fixture 50 that may be used in improved coordinate frame registration and tracking accuracy. The fixture 50 may include one or more marker plates or sheets 52 of radiolucent material, such as an acrylic (e.g., Lexan) or polymer plate. Each sheet holds an array of radiopaque point-like markers 54, such as stainless steel balls (e.g., ball bearings or BBs). The one or more plates holding the BBs may be affixed at or near to the face of the camera imaging assembly so as to allow accurate calibration of the entire volume of interest while occupying a sufficiently small space that the camera may be positioned closely to the patient. The illustrated calibration fixture 50 includes a releasable clamp assembly 51, with a clamp handle 51a, or other attachment device configured to attach directly on or over the face of the camera assembly. Additionally, the calibration fixture 50 may include an attachment point for a tracking sensor. The structure of the calibration fixture 50 is predefined and modeled to serve as a reference. That is, radiopaque markers, sensors, and/or other structures in the calibration fixture 50 are located and measured during manufacturing or prior to use in imaging. Characterization data from the structure of the calibration fixture 50 is used to register the image and navigation coordinate systems. For example, characterization data describing reference markers in the fixture 50 is loaded into a tracking system prior to scanning. Tight manufacturing tolerances and/or modeling are used to model the calibration fixture 50 as a reliable reference to measure and correct registration error.

FIG. 2 illustrates another example of a calibration fixture 60 that may be used in improved coordinate frame registration and tracking accuracy. The calibration fixture 60 may be affixed at or near an object being imaged, such as a patient. The calibration fixture 60 includes an attachment point 61 for a tracking sensor. The calibration fixture 60 includes an array of radiopaque calibration markers, such as BBs. In an embodiment, a size of the second calibration fixture 60 is minimized to reduce an impact of the fixture 60 on a resulting image. Holes or openings, for example, may also be left in the calibration fixture 60, as shown in FIG. 4, to reduce its profile and impact on imaging. The structure of the second calibration fixture 60 is predefined and modeled to serve as a reference. That is, radiopaque markers, sensors, and/or other structures in the calibration fixture 60 are located and measured during manufacturing or prior to use in imaging. Characterization data from the structure of the calibration fixture 60 is used to register the image and navigation coordinate systems. For example, characterization data describing reference markers in the fixture 60 is loaded into a tracking system prior to scanning. Tight manufacturing tolerances and/or modeling are used to model the calibration fixture 50 as a reliable reference to measure and correct registration error.

The BBs or other radiopaque or calibration markers may be of different sizes in the different planes or may be of the same size. In an embodiment, the BBs are of the same size, e.g., about one or two millimeters in diameter. The BBs or other markers appear in an image and are discernable from anatomy or other interesting objects.

In an embodiment, a radiopaque object, such as a metal or other material object, for example a BB, may be placed into holes on a radiolucent marker sheet such that all marker coordinates are known. Alternatively, marker plates may be manufactured by circuit board microlithography techniques to provide desired patterns of radiopaque markers, for example as metallization patterns, on one or more thin radiolucent films or sheets. The calibration fixtures 50, 60 may also be fabricated as a single block of a suitable radiolucent material with holes drilled to accommodate BBs or other markers. BBs or other markers may be arranged at multiple levels and multiple positions in the fixture.

One suitable radiolucent material is a structural foam of the type used in aircraft wings for lightweight structural rigidity. The radiolucent material may also be employed in separate thin marker-holding sheets. In an embodiment, the selected polymer or foam, and the number and size of the markers, are configured to remain directly in the imaging beam of the fluoroscope device and be imaged in each shot, while the position of the fixture is tracked. The fixture materials are selected to avoid introducing any significant level of x-ray absorption or x-ray scattering by the plates, sheets or block, and the size and number of markers are similarly chosen to avoid excessive shadowing of the overall image, while maintaining a sufficiently dense image level for their detectability, so that both the imaging source radiation level and the resulting image density scale remain comparable to currently desired operating levels. In an embodiment, BBs or other markers are arranged in a pattern at one or more levels, with a different pattern at each level. Further, when more than one array at different depths is used, the patterns may be positioned so that as the source/camera alignment changes, BBs of one pattern cast shadows substantially distinct from those of the other pattern(s). Thus, calibration fixtures 50, 60 are predefined structures known with respect to a tracker.

However, use of BBs or other calibration markers in a fixture may impose distortion or artifacts in resulting images. Although some work has been done to remove such artifacts, some distortion still remains, and there is a need for an improved system and method for reducing artifacts introduced in an image by calibration markers. A system and method for improved calibration and distortion reduction would be highly desirable.

Generally, a goal of intrinsic geometry calibration is to determine a location of an x-ray focal spot in relation to an x-ray detector. On existing x-ray systems, such as fixed-room or mobile C-arms, the focal spot location may vary by 10 mm or more over the full range of motion of the C-arm structure. A source of this variation may be elastic deflection of the C-arm itself, bearing backlash, and other component motions. Knowing the precise location of the focal spot is important for 3D reconstruction and 2D navigation.

Fluoroscopy-based 3D imaging and 2D and/or 3D surgical navigation require accurate characterization of imaging parameters such as the camera focal length, piercing point, and optical distortion parameters, etc. Since C-arm devices are mobile imaging equipment, camera calibration is usually performed with every X-ray exposure to compensate for the mechanical deflection of C-arm for different clinical setups. Calibration is typically accomplished by deploying a calibration fixture between the X-ray detector and source that encloses an array of discrete, radiopaque markers such as ball bearings (BBs) arranged in multiple planes. The physical presence of the radiopaque BBs produces shadows on the acquired fluoro-image for estimation of the camera parameters is undesirable for image quality.

Depending on the size and location of the BBs, possible consequences of introducing BBs to the imaging chain include loss of important anatomical features (e.g., 2D cardiovascular imaging), introduction of metal scattering artifacts (e.g., 3D imaging), and bad pixel identification (e.g., flat panel detector IQ).

As mentioned above, prior geometry calibration procedures use a calibration phantom, which typically is comprised of a number of discrete fiducials arranged in a three-dimensional pattern. One such phantom uses a series of BBs arranged in a helix around an x-ray transparent cylinder. In an offline calibration procedure, images of the phantom are acquired throughout the motion trajectory of the C-arm and the intrinsic geometry parameters are computed. These parameters are assumed to remain unchanged and are used for subsequent in vivo scans. Another method uses one or more planes of BBs or crosshairs affixed to the detector surface. This calibration phantom is used clinically. After an image of the anatomy is taken, the intrinsic parameters are calculated and the image artifacts from the fiducials are removed via image processing techniques.

Both of the methods described suffer from disadvantages. The helical phantom and offline procedure assumes that the parameters will remain unchanged. Wear and damage to the device may affect the accuracy of the stored parameters. Furthermore, there may be situations where the user unknowingly is flexing the C-arm by unintended collision with the operating table. The second method suffers from image degradation from the removal of the image artifacts. Also, the depth of the calibration phantom (e.g., 8-10 cm) compromises the usable patient volume between the x-ray source and detector.

Thus, systems and methods that provide intrinsic parameter calculation for a variety of images would be highly desirable. Systems and methods that minimize image degradation would also be highly desirable. Additionally, systems and methods that provide imaging system calibration or characterization without the introduction of markers would be highly desirable.

BRIEF SUMMARY OF THE INVENTION

Certain embodiments of the present invention provide methods and systems for calibration of a camera or other image acquisition device. Certain embodiments provide a system facilitating on-line calibration of an imaging camera. The system includes a first sensor positioned with respect to an imager, a second sensor positioned with respect to an imaging camera and a transmitter positioned with respect to an object to be imaged. A first off-line calibration characterizes a transformation from a coordinate system of the imager to a coordinate system of the first sensor positioned with respect to the imager. A second off-line calibration characterizes a transformation from a coordinate system of the imaging camera to a coordinate system of the second sensor positioned with respect to the imaging camera. Intrinsic parameters of the camera are quantified by a transformation from the coordinate system of the imager to the coordinate system of the imaging camera based on the first and second off-line calibrations and information from the first and second sensors and the transmitter.

Certain embodiments provide a method for calibration of an imaging system. The method includes characterizing a transformation from a coordinate system of an imager to a coordinate system of a first sensor positioned with respect to the imager using a first off-line calibration. The method also includes characterizing a transformation from a coordinate system of an imaging camera source to a coordinate system of a second sensor positioned with respect to the imaging camera source using a second off-line calibration. Additionally, the method includes quantifying intrinsic parameters of the imaging camera source based on a transformation from the coordinate system of the imager to the coordinate system of the imaging camera source based on the first and second off-line calibrations and information from the first and second sensors and a transmitter positioned with respect to an object being imaged.

Certain embodiments provide a computer-readable medium having a set of instructions for execution on a computer. The set of instructions includes a first transformation routine characterizing a transformation from a coordinate system of an imager to a coordinate system of a first sensor positioned with respect to the imager using a first off-line calibration. The set of instructions also includes a second transformation routine characterizing a transformation from a coordinate system of an imaging camera source to a coordinate system of a second sensor positioned with respect to the imaging camera source using a second off-line calibration. Furthermore, the set of instructions includes a camera characterization routine quantifying intrinsic parameters of the imaging camera source based on a transformation from the coordinate system of the imager to the coordinate system of the imaging camera based on the first and second off-line calibrations and information from the first and second sensors and a transmitter positioned with respect to an object being imaged.

Figure 1:
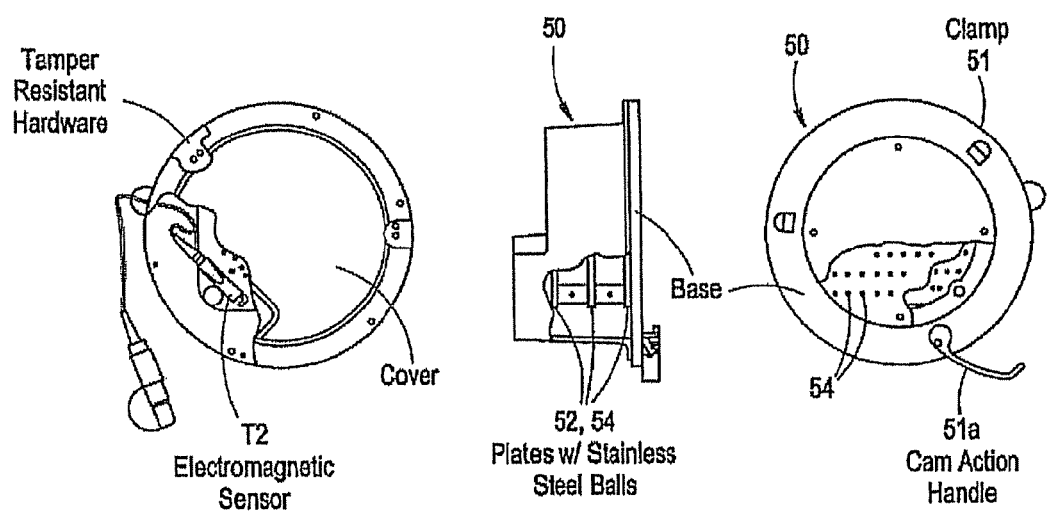
FIG. 1 illustrates an example of a calibration fixture for use in improved coordinate frame registration and tracking accuracy.
Figure 2:
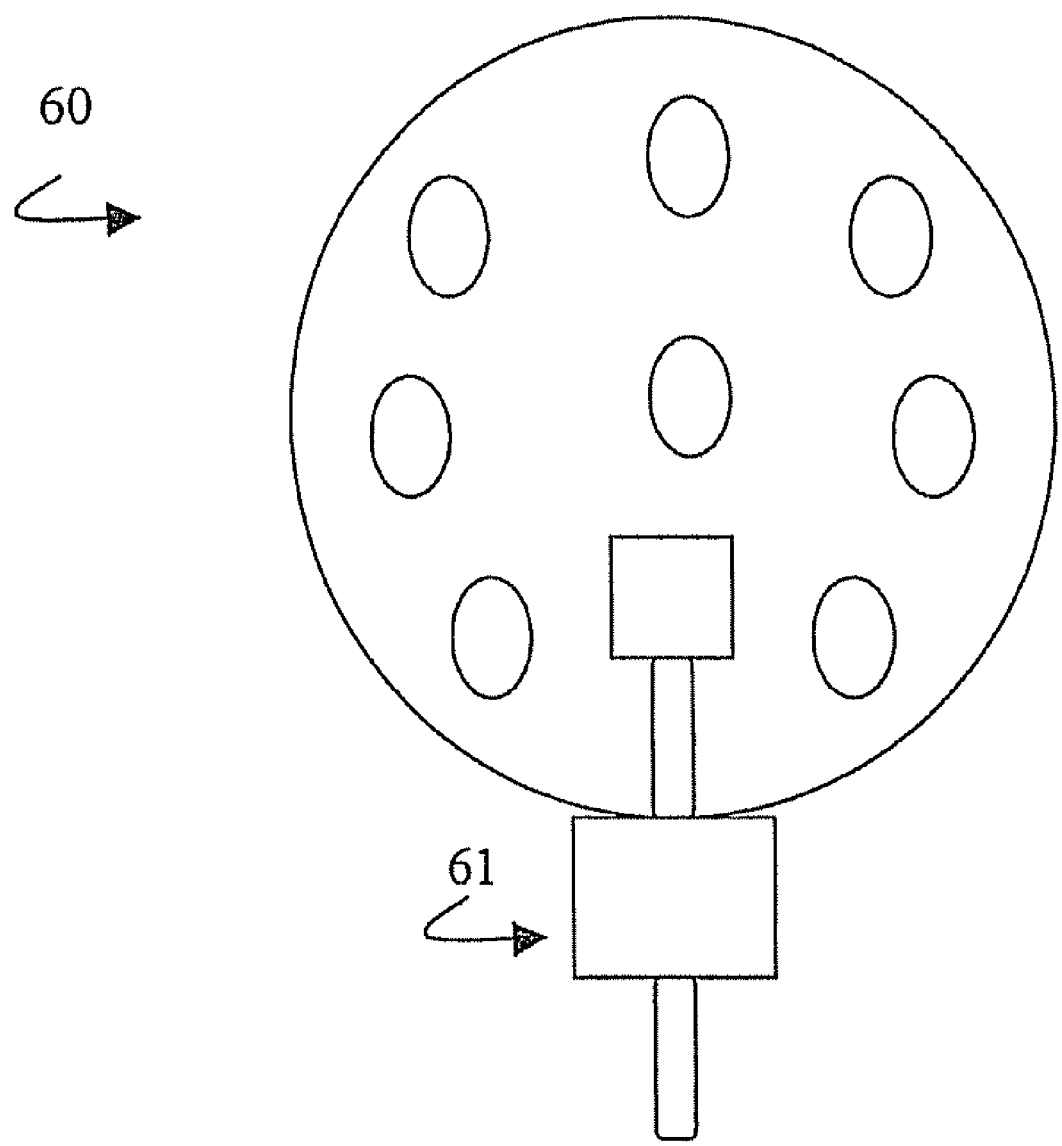
FIG. 2 illustrates another example of a calibration fixture for use in improved coordinate frame registration and tracking accuracy

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 3:
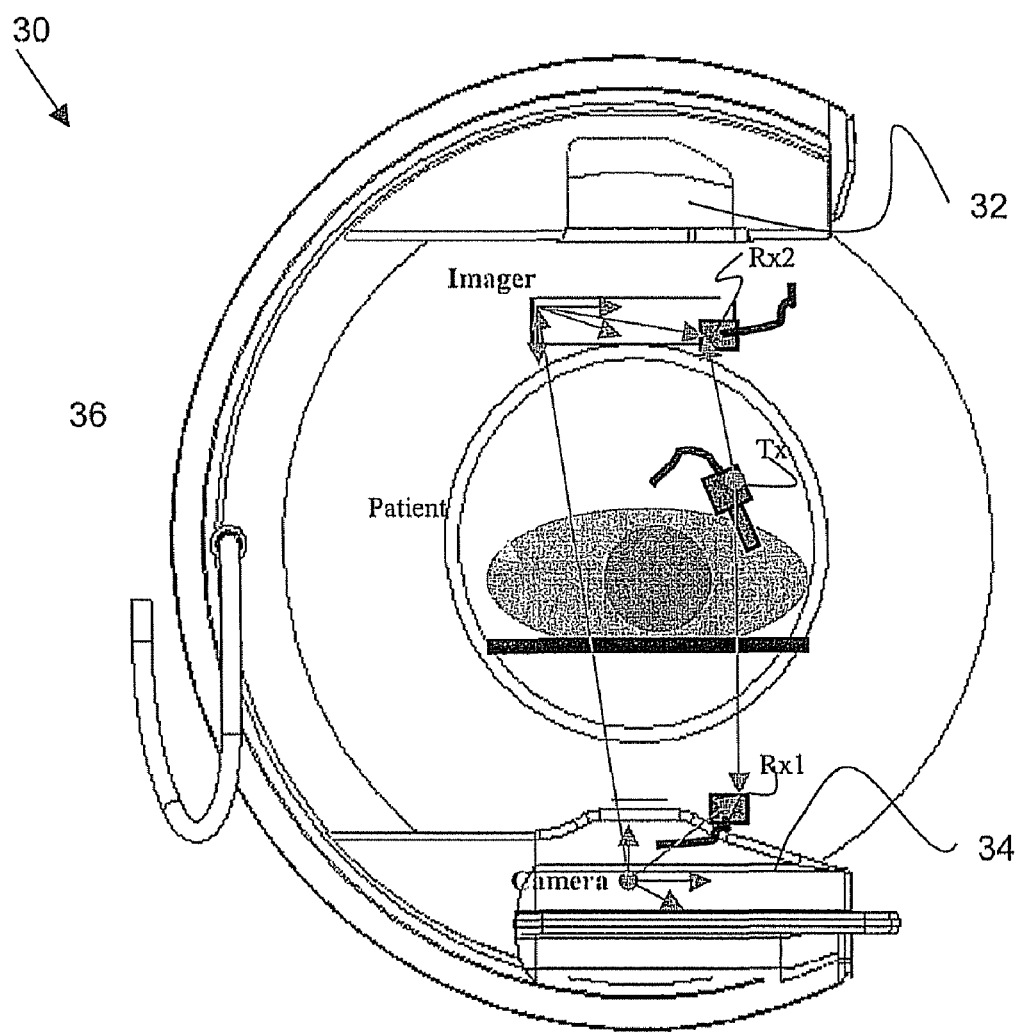
FIG. 3 illustrates an imaging system in accordance with an embodiment of the present invention.

FIG. 3 illustrates an imaging system 30 in accordance with an embodiment of the present invention for use in an operating room environment. As shown in FIG. 3, the camera system 30 includes an imager 32, a camera source 34, a structural support member 36, sensors Rx1 and Rx2, and a transmitter Tx. The imager 32 may be an x-ray detector, for example. The camera source 34 may be an X-ray generator, for example. The structural support member 36 may be a C-arm, L-arm, O-arm and/or other structure supporting the imager 32 and source 34.

For example, the imager 32 may be mounted on the structural support member 36 opposite the camera source 34. The support member 36 moves about a patient or other object to produce two dimensional projection images of the patient from different angles. The patient or object remains positioned between the imager 32 and the source 34, and may, for example, be situated on a table or other support, although the patient/object may move.

Sensor Rx1 is positioned with respect to the camera source 34 (e.g., camera sensor Rx1). For example, the sensor Rx1 is affixed to or otherwise mounted on the source 34. Sensor Rx2 is positioned with respect to the imager 32 (e.g., imager sensor Rx2). For example, the sensor Rx2 is affixed to or otherwise mounted on the imager 32. Transmitter Tx is positioned with respect to an instrument, such as a probe or surgical tool, or with respect to a patient or other object. The instrument may be rigid, allowing the transmitter Tx to be fixed at a known or convenient position, such as on its handle. Alternatively, the tool may be a flexible tool, such as a catheter, flexible endoscope or an articulated tool, for example. In the latter cases, the transmitter Tx is preferably a small, localized element positioned in or at the operative tip of the tool to track coordinates of the tip within the body of the patient.

In an embodiment, the system 30, such as a fluoroscope system, operates with the imager 32 positioned opposite the X-ray source or generator 34. While in some systems, the imager 32 is fixed overhead and the source 34 is located below a patient support, the discussion below will be illustrated with regard to the more complex case of a typical C-arm fluoroscope, in which the imager or detector 32 and source 34 are connected by the structural support member 36, such as a C-arm, that allows movement of the imager 32 and camera source assembly 34 about the patient so that the C-arm may be positioned to produce x-ray views from different angles or perspectives. In such C-arm devices, the imaging beam generally diverges at an angle, the relative locations and orientations of the imager 32 and source 34 vary with position due to structural flexing and mechanical looseness, and the position of both the imager 32 and the source 34 with respect to the patient and/or a tool which it is desired to track may also vary in different shots.

Figure 4:
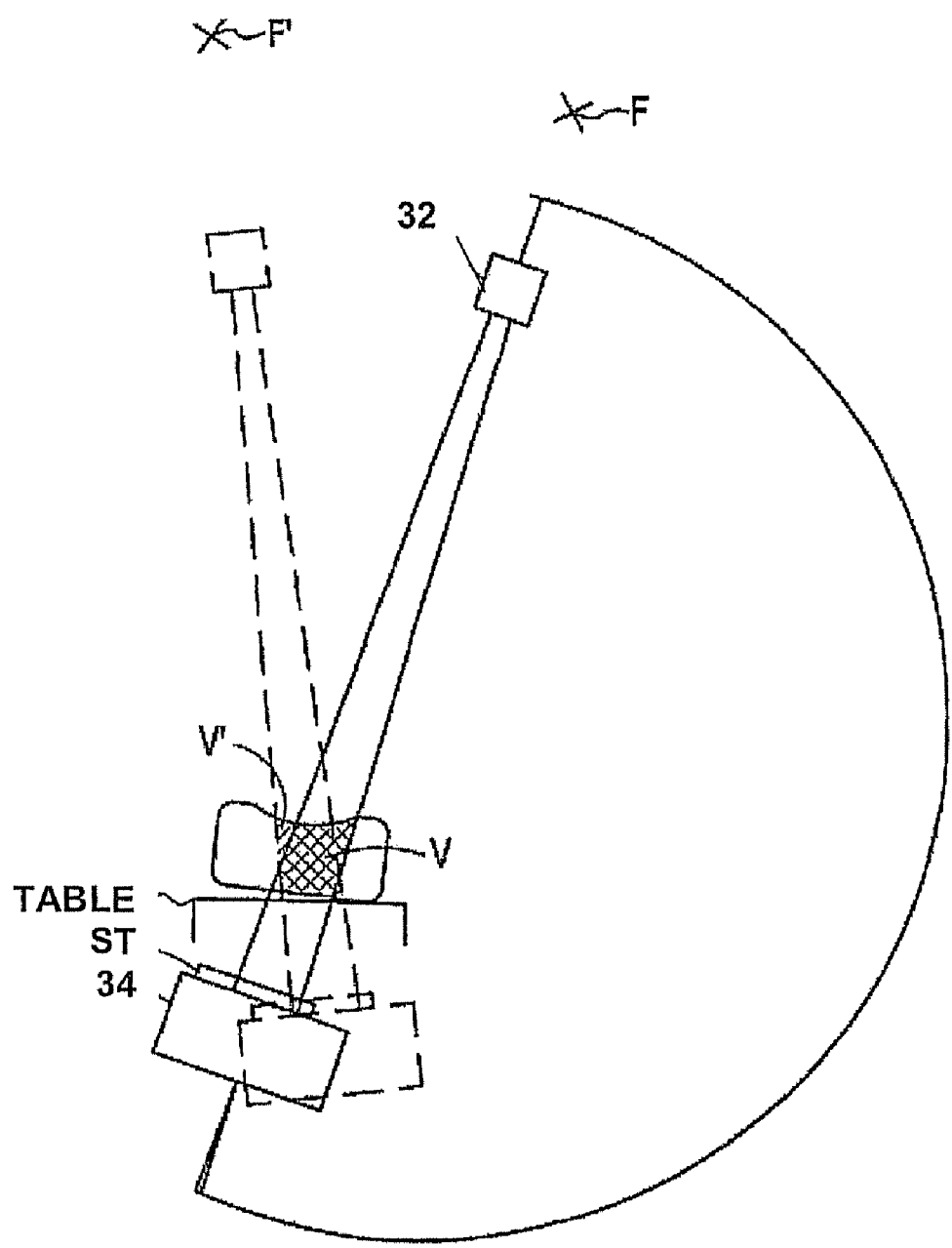
FIG. 4 illustrates a fluoroscope in two different imaging positions, with a first position shown in solid line, and a second position in dashed line phantom.

FIG. 4 illustrates the system 30 in two different imaging positions, with a first position shown in solid line, and a second position in dashed line phantom. In the first position, a tissue volume V is imaged with a divergent beam from the above right, and a virtual beam origin or focal point at F, while the image from the second position catches a largely overlapping but partly distinct tissue volume with a divergent beam from the upper left, and a different focal point F. The distances from points F, F to the camera may be different, and the camera itself may shift and tilt with respect to the beam and its center axis, respectively. In practice, the x-ray beam is generally aimed by its center ray, whose intersection with the imaging plane, referred to as the piercing point, may be visually estimated by aiming the assembly with a laser pointing beam affixed to the source. The x-ray beam may be considered to have a virtual origin or focal point F at the apex of the cone beam. Generally, the imager assembly 32 is positioned close to the patient, but may be subject to constraints posed by the operating table, the nature of the surgical approach, and tools, staging, clamps and the like, so that imaging of a tissue volume somewhat off the beam center line, and at different distances along the beam, may occur. As noted above, flexing of the C-arm or other support member 36 also changes the distance to the focal point F and this also may slightly vary the angular disposition of the beam to the camera source 34, so this shifting geometry may affect the fluoroscope images.

Furthermore, the camera source 34 may utilize an image sensing unit that itself introduces further distortions into the received distribution of image radiation. For example, the unit may involve a detector that employs a phosphor surface of generally curved contour to convert the x-ray image intensity distribution to a free electron distribution. Such a curved phosphor screen is generally placed over an electron multiplier or image intensifier assembly that provides an enhanced output video signal, but may further introduce a form of electron optical distortion that depends upon the intensifier geometry and varies with the orientation of the camera assembly in the earth's magnetic field. Other configurations of image detectors are also known or proposed, such as digital x-ray detectors or flat semiconductor arrays, which may have different imaging-end fidelity characteristics. Deflection or physical movement of the camera itself as well as electron/optical distortion from the camera geometry, image detector and variations due to gravitational, magnetic or electromagnetic fields may enter image reception and affect projective geometry and other distortion of a final image produced by the assembly.

In an embodiment, camera characterization is determined separately from navigation, such as electromagnetic (EM) tracking. That is, sensors Rx1, Rx2 and transmitter Tx may be used concurrently and/or sequentially for camera characterization and tracking. A tracking system may track the camera and/or track the object being imaged to characterize (i.e., extract) camera parameters. The position of the object relative to the sensor may be determined by the tracking system in order to track the sensor during an image-guided operation.

In certain embodiments, at least one position sensor Rx2 is rigidly attached to the imager 32, and at lest one sensor Rx1 is attached to the camera source 34. Sensors Rx1 and Rx2 may be electromagnetic sensors, optical sensors, or other types of sensors to track the change of camera imaging parameters. Sensors Rx1 and Rx2 may be integrated into the imaging system (e.g., a C-arm imaging system) to enable dynamic tracking of support member (e.g., C-arm or other support/positioning member) deflection at an arbitrary position.

Calibration of camera intrinsic parameters (e.g., focal length and image plane with respect to camera coordinate) corresponds to finding a transformation from an imager space to a camera space. The origin of the camera coordinate system is usually defined at the center of the camera source. For example, a transformation between the imager 32 and the camera source 34, $^{Imager}T_{Cam}$, may be represented as follows:

$$^{Imager}T_{Cam} = {}^{Imager}T_{Rx2} {}^{Rx2}T_{Tx} {}^{Tx}T_{Rx1} {}^{Rx1}T_{Cam} \quad \text{(Eq. 1)}.$$

In Equation 1, $^{Imager}T_{Rx2}$ is a "fixed" coordinate system transformation (CST) from the imager coordinate system to the sensor Rx2 coordinate system. Variables $^{Rx2}T_{Tx}$ and $^{Tx}T_{Rx1}$ are dynamic CSTs provided by tracking information from sensors Rx1 and Rx2 and transmitter Tx. $^{Rx1}T_{Cam}$ is a "fixed" CST from the detector or camera coordinate system to sensor Rx1 coordinate system.

Both $^{Imager}T_{Rx2}$ and $^{Rx1}T_{Cam}$ may be characterized via a one-time, off-line camera calibration. The off-line calibration may be performed at a single, arbitrary camera position. No calibration for multiple C-arm positions may be needed. However, if desired, the calibration may be repeated for multiple positions.

Figure 5:
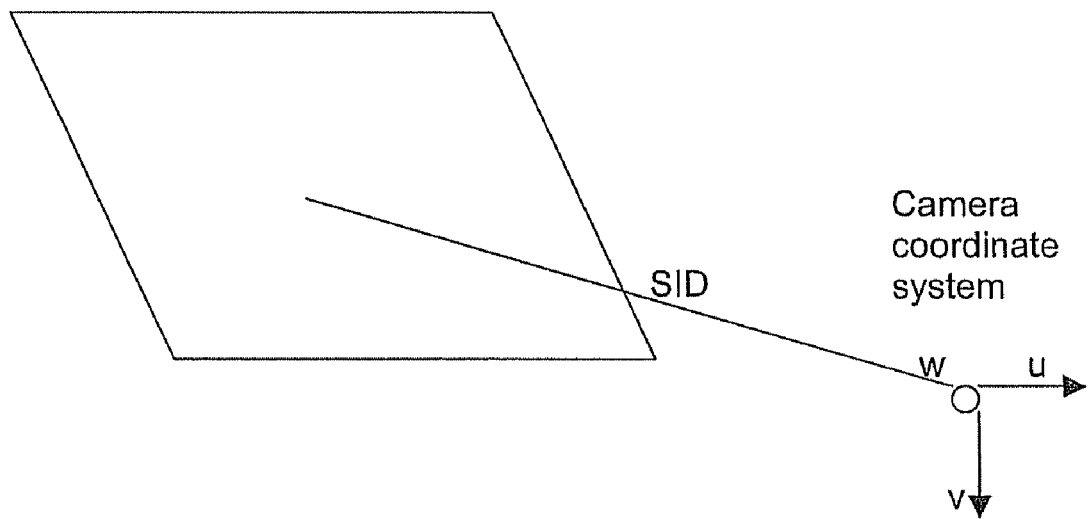
FIG. 5 illustrates an example of the camera coordinate system with respect to the source.

In certain embodiments, a principal point {u0, v0} may be defined for plane coordinates of an intersection of a central x-ray beam and detector plane. A source-to-imager distance (SID) represents a distance from a source to the detector plane along the central x-ray beam, for example. Quantities are defined in the camera coordinate system {U, V, W}. The camera coordinate system describes the relative geometry of the detector 32 and the source 34. FIG. 5 illustrates an example of the camera coordinate system with respect to the source. Causes of variation in parameters may include component manufacturing defects, mounting imperfectness, deflection due to weight force, environmental interference, etc.

In certain embodiments, the principle point and SID may be determined using cone-beam projection geometry. The principle point {u0, v0} is defined as the most probably intersection of x-ray pathways, for example. Planes P and Q are defined to intersect at the principle point. Centroids of the plans P and Q in the imager plane may be represented as $\{u^p_1, v^p_1\}$ and $\{u^q_1, v^q_1\}$, respectively. The centroid coordinates $\{u^p_1, v^p_1\}$ and $\{u^q_1, v^q_1\}$ are known a priori, for example. The centroids of segmented shadow, P' and Q', have coordinates $\{u^p_1, v^p_1\}$ and $\{u^q_1, v^q_1\}$, correspondingly. Coordinates of the intersection of lines |PP'| and |QQ'| may be determined as follows:

$$u_0 = (b^q - b^p)/(a^p - a^q) \quad \text{(Eq. 2),}$$

$$v_0 = (b^q a^p - b^p a^q)/(a^p - a^q) \quad \text{(Eq. 3),}$$

with $$a^t = -(v^t_2 - v^t_1)/(u^t_2 - u^t_1) \quad \text{(Eq. 4)}$$

$$b^t = -(v^t_2 u^t_1 - v^t_1 u^t_2)/(u^t_2 - u^t_1), t=p,q \quad \text{(Eq. 5)}.$$

For N points derived from the delineation of an intersection of N line pairs, mean and standard deviation values become $$\overline{\{u_0, v_0\}} = \underset{j=1\ldots N}{\text{mean}} \{u_0, v_0\}j, \quad \text{(Eq. 6)}$$

$$\Delta\{u_0, v_0\} = \underset{j=1\ldots N}{\text{std}} \{u_0, v_0\}j. \quad \text{(Eq. 7)}$$

Figure 6:
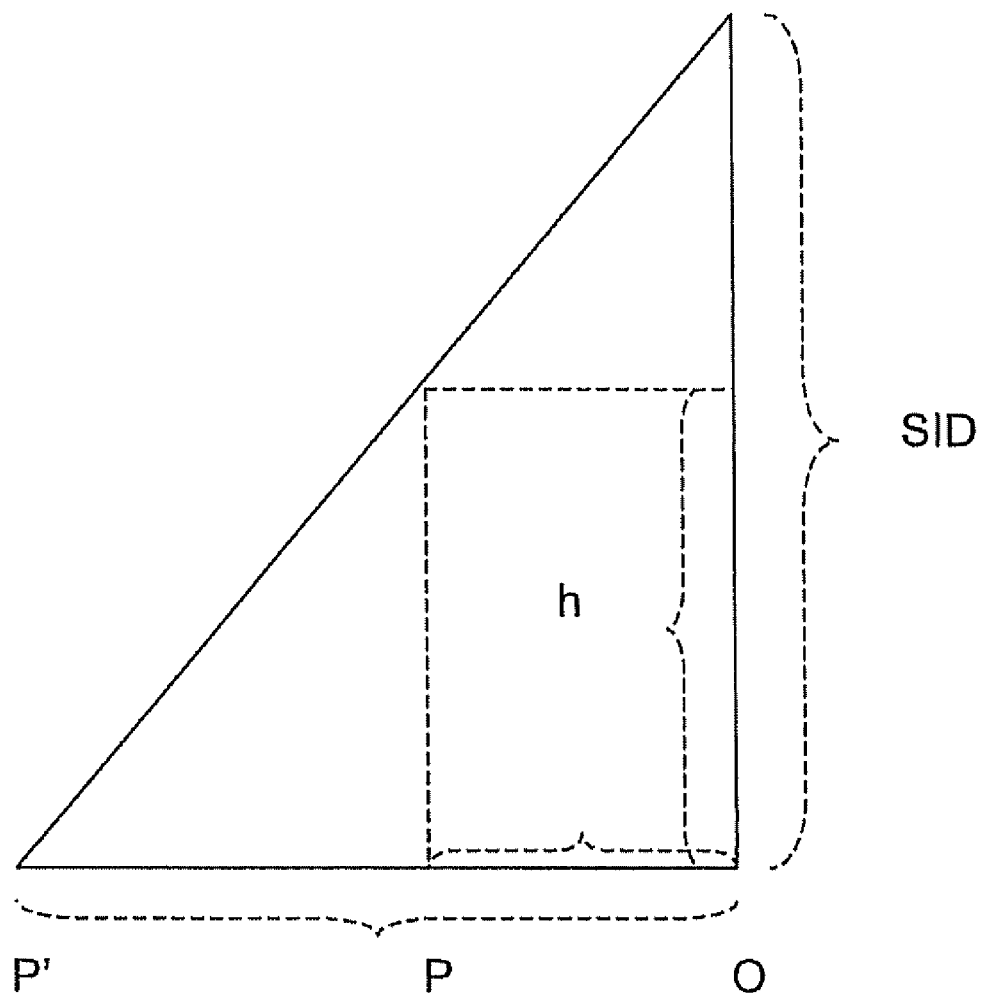
FIG. 6 shows a relationship between a principal point O and a plane P'.

The principal point may then be represented as point O. Then, SID may be determined geometrically by finding the length of a side of a triangle with base |OP'|. See FIG. 6, for example. Using principal point, O, and a known height, h, a proportion may be constructed as follows:

$$\frac{SID}{h} = \frac{norm(\overline{OP'})}{norm(\overline{OP})} = \frac{\sqrt{(u_2^p - u_0)^2 + (v_2^p - v_0)^2}}{\sqrt{(u_1^p - u_0)^2 + (v_1^p - v_0)^2}}.$$ (Eq. 8)

For SIDs derived from delineation of N triangles, the mean and standard deviation values become $$\overline{SID} = \text{mean}\, j = 1 \ldots N\{SID\}j,$$ (Eq. 9)

$$\Delta SID = \underset{j=1 \ldots N}{std}\{SID\}j.$$ (Eq. 10)

Using the principal point and SID, the CST between the imager 32 and sensor Rx2 and the CST between the camera source 34 and sensor Rx1 may be characterized.

Thus, $^{Imager}T_{Rx2}$ and $^{Rx1}T_{Cam}$ are fixed or constant, within a reasonable tolerance, values representing distances or relationships between the imager 32 and sensor Rx2 and between the camera source 34 and sensor Rx1. Transformation $^{Imager}T_{Rx2}$ allows a coordinate or positional transformation from the imager 32 coordinate system to the sensor Rx2 coordinate system. Transformation $^{Rx1}T_{Cam}$ allows a coordinate or positional transformation from the camera 34 coordinate system to the sensor Rx1 coordinate system. Since the sensors Rx1 and Rx2 are statically positioned, the sensors and the corresponding distances/relationships between the sensors Rx1, Rx2 and the camera source 34 and imager 32, respectively, should not appreciably change.

Transformations $^{Rx2}T_{Tx}$ and $^{Tx}T_{Rx1}$ provide dynamic coordinate system transformations based on information generated by the transmitter Tx and received by the sensors Rx1 and Rx2. By storing values for static transformations $^{Imager}T_{Rx2}$ and $^{Rx1}T_{Cam}$ and gathering tracking data for transformations $^{Rx2}T_{Tx}$ and $^{Tx}T_{Rx1}$, Equation (1) may be solved to determine at transformation from the imager 32 coordinate system to the camera 34 coordinate system. Thus, the camera system 30 may be calibrated on-line without use of markers or other fiducials.

Figure 7:
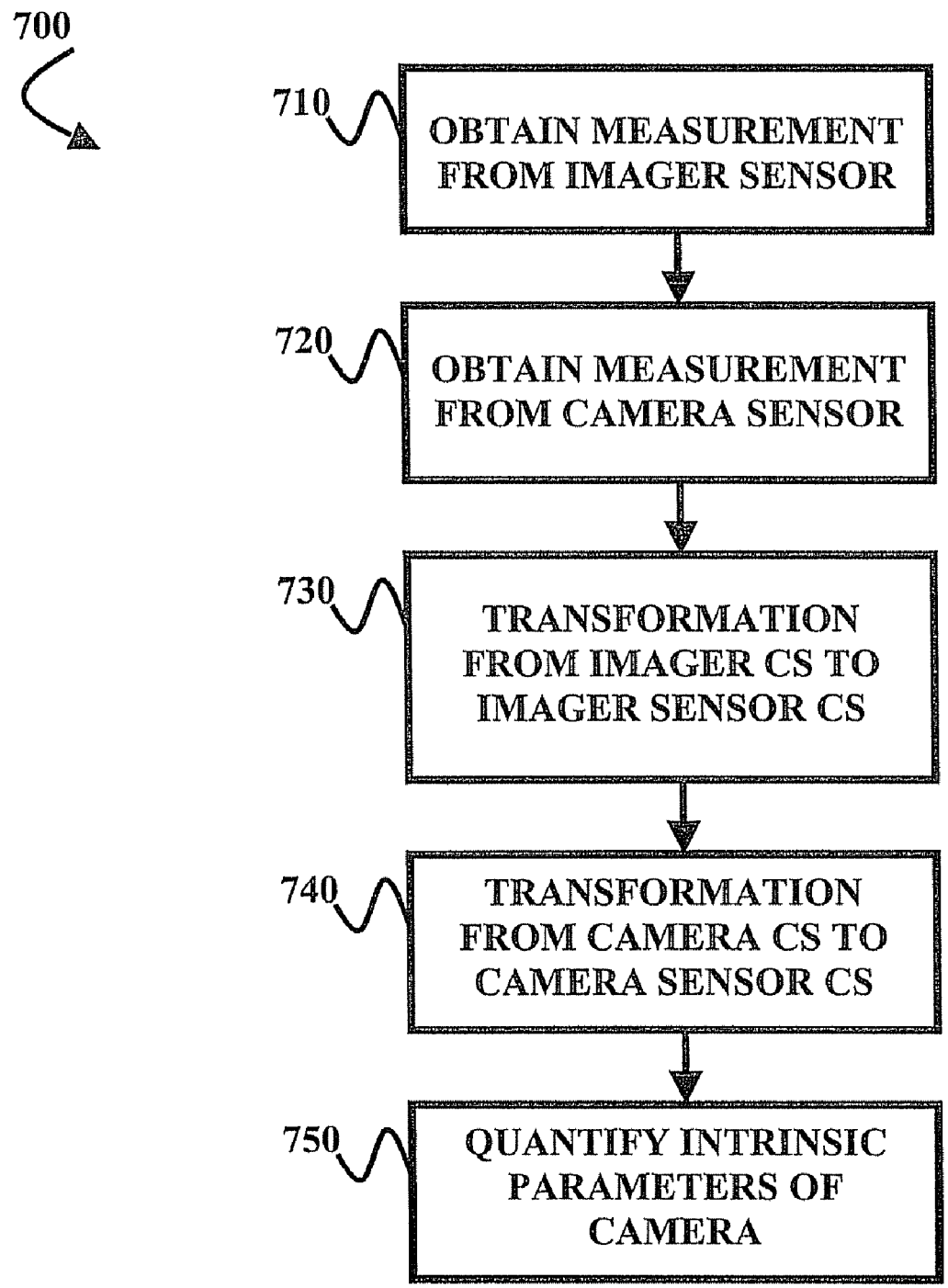
FIG. 7 illustrates a flow diagram for a method for improved characterization of an imaging camera used in accordance with an embodiment of the present invention.

FIG. 7 illustrates a flow diagram for a method 700 for improved characterization of an imaging camera used in accordance with an embodiment of the present invention. At step 710, a measurement from a sensor positioned in relation to the imager is obtained. For example, a position measurement from a sensor rigidly attached to an x-ray imager is obtained. At step 720, a measurement from a sensor positioned in relation to the camera is obtained. For example, a position measurement from a sensor attached to the x-ray source end of a C-arm is obtained.

At step 730, a transformation from the coordinate system of the imager to the coordinate system of the sensor attached to the imager is characterized. For example, transformation $^{Imager}T_{Rx2}$ is characterized using a one-time, off-line camera calibration. At step 740, a transformation from the coordinate system of the camera to the coordinate system of the sensor attached to the camera or camera housing. For example, transformation $^{Rx1}T_{Cam}$ is characterized using a one-time, off-line camera calibration.

At step 750, intrinsic parameters of the camera may be quantified by finding the transformation from the coordinate system of the imager to the coordinate system of the camera, $^{Imager}T_{Cam}$, as shown in Equation (1). Additional characterization data may be obtained from a transmitter and one or more receivers in the imaging system, as well as the transformations $^{Imager}T_{Rx2}$ and $^{Rx1}T_{Cam}$ described above.

Thus, an imaging system camera is characterized using data obtained from the tracking devices in the imaging system. That is, the camera, as well as relationships between camera, imager, sensors and transmitter, may be modeled. Coordinates in a camera or image coordinate system and a navigation or tracking coordinate system may be correlated using characterization data. Thus, the imaging system may be calibrated for imaging and image-guided operations.

After characterization/calibration, one or more images of the object may be obtained using the imaging system. Obtained images may be viewed by an operator, such as a surgeon. If desired, the images may be "cleaned up" to remove distortion or other artifact. Characterization of the method 700 may be repeated before each imaging session and/or between images, depending upon circumstances and/or operator instructions, for example.

Thus, certain embodiments provide navigation-based, "marker-less" systems and methods for on-line camera calibration. Certain embodiments eliminate presence of fiducials in the imaging chain while maintaining the on-line camera calibration capability in compensating non-repeatable C-arm deflection.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system facilitating on-line calibration of an imaging camera, said system comprising:
   a first sensor positioned with respect to an imager;
   a second sensor positioned with respect to a camera source; and
   a transmitter positioned with respect to an object to be imaged that transmits tracking data to said first and second sensors during said on-line calibration,
   wherein a first off-line calibration characterizes a transformation from a coordinate system of said imager to a coordinate system of said first sensor positioned with respect to said imager and a second off-line calibration characterizes a transformation from a coordinate system of said camera source to a coordinate system of said second sensor positioned with respect to said camera source, and
   wherein intrinsic parameters of said camera source are quantified by a transformation from the coordinate system of said imager to the coordinate system of said camera source based on said first and second off-line calibrations and said tracking data.

2. The system of claim 1, wherein said first and second sensors and said transmitter comprise electromagnetic first and second sensors and transmitter.

3. The system of claim 1, wherein said intrinsic parameters of said camera source are quantified by a transformation $^{Imager}T_{Cam} = {}^{Imager}T_{Rx2} \cdot {}^{Rx2}T_{Tx} \cdot {}^{Tx}T_{Rx1} \cdot {}^{Rx1}T_{Cam}$, wherein $^{Imager}T_{Rx2}$ is a coordinate system transformation from the coordinate system of said imager to the coordinate system of said first sensor, $^{Rx1}T_{Cam}$ is a coordinate system transformation from the coordinate system of said camera source to the coordinate system of said second sensor, and $^{RX2}T_{Tx}$ and $^{Tx}T_{Rx1}$ are dynamic coordinate system transformations provided by tracking information from said first and second sensors and said transmitter.

4. The system of claim 1, wherein at least one of said imager and said camera source are mounted on a support member.

5. The system of claim 4, wherein said support member comprises at least one of a C-arm, an L-arm and an O-arm.

6. The system of claim 4, wherein said first and second sensors and said transmitter dynamically track deflection of said support member.

7. The system of claim 1, wherein said first and second sensors and said transmitter obtain at least one of position and orientation data for said object.

8. The system of claim 1, wherein said first and second off-line calibrations are performed at a single arbitrary camera position.

9. The system of claim 1, wherein said on-line calibration is performed without using markers.

10. A method for calibration of an imaging system, said method comprising:
    characterizing a transformation from a coordinate system of an imager to a coordinate system of a first sensor positioned with respect to said imager using a first off-line calibration;
    characterizing a transformation from a coordinate system of an imaging camera source to a coordinate system of a second sensor positioned with respect to said imaging camera source using a second off-line calibration; and
    quantifying intrinsic parameters of said imaging camera source based on a transformation from the coordinate system of said imager to the coordinate system of said imaging camera source based on said first and second off-line calibrations and tracking data transmitted from a transmitter positioned with respect to an object being imaged to said first and second sensors during an on-line calibration.

11. The method of claim 10, wherein said quantifying step further comprises quantifying intrinsic parameters of said imaging camera source based a transformation $^{Imager}T_{Cam} = {}^{Imager}T_{Rx2} \cdot {}^{Rx2}T_{Tx} \cdot {}^{Tx}T_{Rx1} \cdot {}^{Rx1}T_{Cam}$, wherein $^{Imager}T_{Rx2}$ is a coordinate system transformation from the coordinate system of said imager to the coordinate system of said first sensor, $^{Rx1}T_{Cam}$ is a coordinate system transformation from the coordinate system of said imaging camera source to the coordinate system of said second sensor, and $^{Rx2}T_{TX}$ and $^{Tx}T_{Rx1}$ are dynamic coordinate system transformations provided by tracking information from said first and second sensors and said transmitter.

12. The method of claim 10, wherein at least one of said imager and said imaging camera source are mounted on a support member.

13. The method of claim 12, wherein said first and second sensors and said transmitter dynamically track deflection of said support member.

14. The system of claim 10, wherein said first and second sensors and said transmitter obtain tracking data related to said object.

15. The method of claim 10, wherein said first and second off-line calibrations are performed at a single arbitrary camera position.

16. The method of claim 10, further comprising modeling said imaging camera source based on said intrinsic parameters.

17. The method of claim 10, wherein said on-line calibration is performed without using markers.

18. A non-transitory computer-readable medium having a set of instructions for execution on a computer, said set of instructions comprising:
    a first transformation routine characterizing a transformation from a coordinate system of an imager to a coordinate system of a first sensor positioned with respect to said imager using a first off-line calibration;
    a second transformation routine characterizing a transformation from a coordinate system of an imaging camera source to a coordinate system of a second sensor positioned with respect to said imaging camera source using a second off-line calibration; and
    a camera characterization routine quantifying intrinsic parameters of said imaging camera source based on a transformation from the coordinate system of said imager to the coordinate system of said imaging camera source based on said first and second off-line calibrations and tracking data transmitted from a transmitter positioned with respect to an object being imaged to said first and second sensors during an on-line calibration.

19. The set of instructions of claim 18, wherein said camera characterization routine quantifies intrinsic parameters of said imaging camera source based a transformation $^{Imager}T_{Cam} = {}^{Imager}T_{Rx2} \cdot {}^{Rx2}T_{Tx} \cdot {}^{Tx}T_{Rx1} \cdot {}^{Rx1}T_{Cam}$, wherein $^{Imager}T_{Rx2}$ is a coordinate system transformation from the coordinate system of said imager to the coordinate system of said first sensor, $^{Rx1}T_{Cam}$ is a coordinate system transformation from the coordinate system of said imaging camera source to the coordinate system of said second sensor, and $^{Rx2}T_{Tx}$ and $^{Tx}T_{Rx1}$ are dynamic coordinate system transformations provided by tracking information from said first and second sensors and said transmitter.

20. The set of instructions of claim 18, wherein said first and second off-line calibrations are performed at a single arbitrary camera position.

21. The set of instructions of claim 18, further comprising a modeling routine for modeling said imaging camera source based on said intrinsic parameters.

22. The set of instructions of claim 18, further comprising a tracking routine using said first and second sensors and said transmitter to dynamically track deflection of a support member upon which at least one of said imager and said imaging camera source are mounted.

23. The set of instructions of claim 18, wherein said on-line calibration is performed without using markers.

* * * * *

UNITED STATES PATENT AND TRADEMARK OFFICE
CERTIFICATE OF CORRECTION

PATENT NO. : 8,350,914 B2  
APPLICATION NO. : 13/101776  
DATED : January 8, 2013  
INVENTOR(S) : Li et al.

Page 1 of 1

It is certified that error appears in the above-identified patent and that said Letters Patent is hereby corrected as shown below:

In the Specification:

In Column 5, Line 55, delete "scanning" and insert -- scanning. --, therefor.

In Column 9, Line 67, delete "accuracy" and insert -- accuracy. --, therefor.

In Column 11, Line 15, delete "F." and insert -- F'. --, therefor.

In Column 11, Line 16, delete "F, F" and insert -- F, F' --, therefor.

In Column 11, Line 63, delete "lest" and insert -- least --, therefor.

Signed and Sealed this  
Twenty-ninth Day of October, 2013

Teresa Stanek Rea  
*Deputy Director of the United States Patent and Trademark Office*